United States Patent [19]

de Haan

[11] 4,041,060

[45] Aug. 9, 1977

[54] PROCESS FOR SYNTHESIZING ORGANO-TIN COMPOUNDS

[76] Inventor: Andre Paul de Haan, Avenue Lemiez, 35 - B 7020 Hyon, Belgium

[21] Appl. No.: 674,537

[22] Filed: Apr. 7, 1976

Related U.S. Application Data

[63] Continuation-in-part of Ser. No. 564,978, April 3, 1975, abandoned.

[30] Foreign Application Priority Data

Apr. 3, 1974 Belgium .................................. 142797

[51] Int. Cl.$^2$ ............................................. C07F 7/22
[52] U.S. Cl. .................................................... 260/429.7
[58] Field of Search ........................................ 260/429.7

[56] References Cited

U.S. PATENT DOCUMENTS

| | | | |
|---|---|---|---|
| 2,625,559 | 1/1953 | Smith | 260/429.7 |
| 2,679,505 | 5/1954 | Weinberg | 260/429.7 |
| 2,679,506 | 5/1954 | Rochow | 260/429.7 |

FOREIGN PATENT DOCUMENTS

| | | |
|---|---|---|
| 1,046,052 | 12/1958 | Germany |

OTHER PUBLICATIONS

Smith et al., J.A.C.S. V75, pp. 4103–4106, (1953).

*Primary Examiner*—Helen M. S. Sneed
*Attorney, Agent, or Firm*—Sughrue, Rothwell, Mion, Zinn and Macpeak

[57] ABSTRACT

This invention relates to a process for synthesizing organo-tin halides by reacting an organic halide of the formula RX wherein R represents an organic, preferably alkyl or aryl radical whereas X represents halogen, with a finely divided solid alloy, consisting of tin and a catalyst of the class consisting of copper, gold and silver, so as to form a compound of the formula $R_n Sn X_{4-n}$ wherein R and X have the meanings indicated here-above and n represents an integer equal to 1, 2 or 3 wherein any contact of alloy particles with one another is avoided by separating said particles in a fluidized bed by means of a fluid comprising said organic halide, by admixing refractory particles to the alloy particles and by stirring thoroughly the fluidized bed.

The products made according to the invention are particularly useful for stabilizing chlorinated organic materials.

8 Claims, 1 Drawing Figure

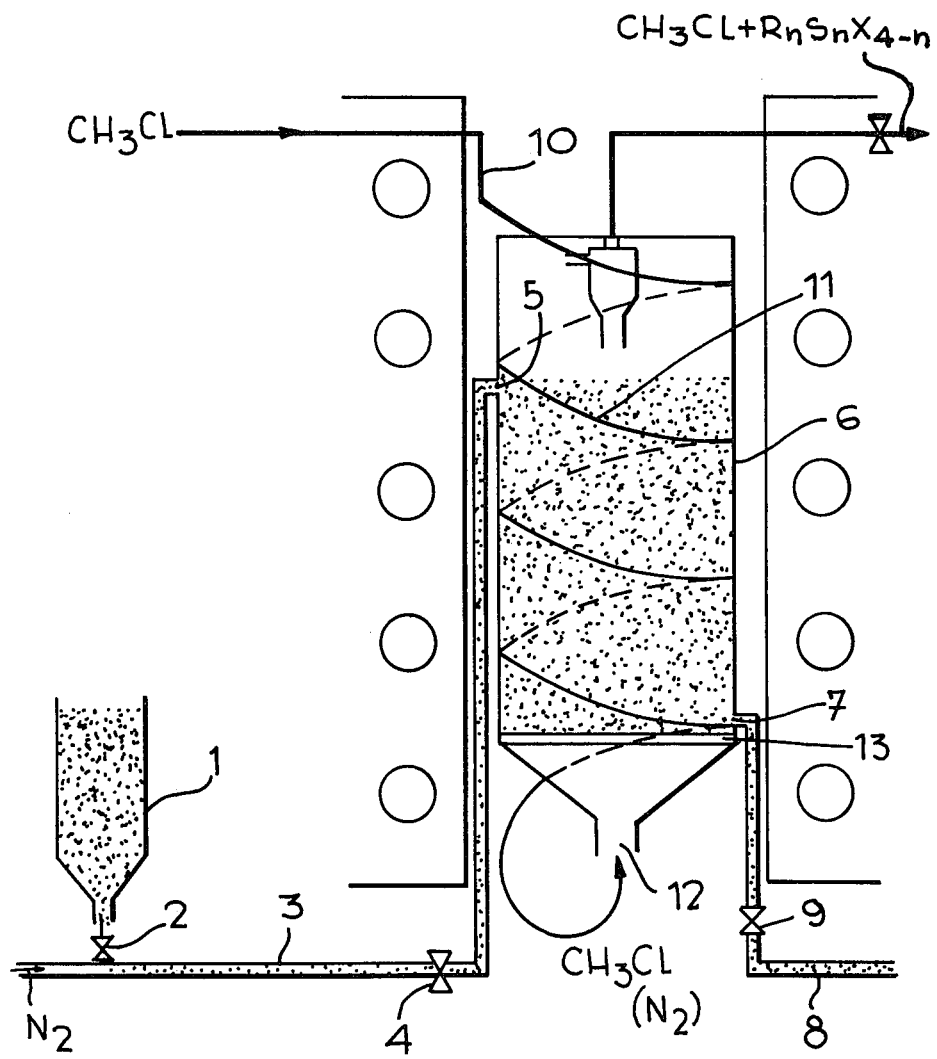

PROCESS FOR SYNTHESIZING ORGANO-TIN COMPOUNDS

This application is a continuation-in-part of U.S. Ser. No. 564,978 filed Apr. 3, 1975, now abandoned.

BACKGROUND OF THE INVENTION

The present invention relates to a process for the synthesis of organo-tin halides.

Organo-tin halides prepared according to this invention may be represented by the general formula $R_n Sn X_{4-n}$, wherein R is an alkyl or aryl group. Sn is the symbol of tin and X is a halogen. Th alkyl group may be cyclic.

Organo-tin halides of the kind described are particularly useful in stabilizing chlorinated organic materials such as resins of vinyl chloride, chlorinated paraffins, etc. They are, in addition, particularly suitable for the heat surface treatment of glass used in making bottles or flasks to which they impart outstanding surface properties by increasing the mechanical strength and reducing the frictions. This type of treatment permits to diminish the weight of the bottles while keeping a good resistance to shocks.

SUMMARY OF THE INVENTION

The invention has for its object a process for synthesizing organo-tin halides by a straightforward process in which an organic halide of the formula RX is put in the presence of a finely divided solid consisting of tin and a catalyst of the class consisting of copper, gold and silver, to form the compound $R_n Sn X_{4-n}$.

The process described aims to avoid the kinetics restrictions and risks which are encountered in known industrial plants where the straightforward synthesis is made in a fixed bed of great height. The total kinetics of production is then very slow because after the first minutes of reaction the particles made of tin alloy adhere to one another as a result of the exothermic character of the reaction. This results in a caking of the whole particle bed wherein the gas consisting of alkyl (or aryl) halide takes preferred ways in which tin is quickly exhausted. Under these circumstances, the entire bed is only fed by diffusion which strongly limits the velocity of the reaction process. In addition, desorption of the reaction products is very difficult. That effect extends even more the duration of reaction and in the alloy body there always remains an amount of reaction product of 5 to 10% which cannot be recovered. Finally, after reaction, the alloy essentially consisting of copper is very difficult to recover without breaking the reactor.

The basic principle of the process according to the invention is to create suitable conditions for avoiding the contact of the particles with one another by separating them by means of a fluid comprising the organic halide mixed with an inert gas such as nitrogen in a fluidised bed. Although the density of the alloy is situated in a range wherein fluidization is not applied, it has proved perfectly feasible by experience.

According to the invention the contact of the alloy particles is further avoided by admixing to the alloy particles an amount of refractory particles and by intensively stirring the fluidised bed.

In a specific embodiment of the invention the process is applied to the synthesis of dimethyl-dichloro-stannane $(CH_3)_2 Sn Cl_2$, thereby using as the gaseous reagent methylchloride.

In a further specific embodiment of the invention the used tin alloys consist of copper-tin alloys having tin contents ranging from about 40% to about 60% by weight or even more.

According to a particular feature of the invention the reaction is performed at a temperature comprised between 300° and 400° C preferably about 350° C.

According to another particular feature the alloy particles have sizes comprised between 50 and 250 microns.

According to still another particular feature the refractory particles are constituted of sand, silica, alumina, etc. Because of the very great difference of density between refractory particles (d = 1,5 - 2,5) and alloy particles (d = about 9) their particle size ratio should be kept such that any segregation in the bed is avoided in operation.

DESCRIPTION OF THE DRAWING

Hereafter the invention is described referring to the accompanying drawing wherein FIG. 1 is a schematic representation of a fluidised bed reactor.

In FIG. 1, for synthesizing in a fluidized bed, copper-tin alloy and silica are fed from a hopper 1, through a valve 2, to a feeding line 3 with a valve 4. The stream of gas and solid particles enters at 5 at the upper part of the reactor 6, falls down in the reactor, goes out at 7 and is removed through a line 8 with a valve 9. In the reactor, said stream meets in counter-current the organic halide, e.g. $CH_3Cl$, fed through a line 10, pre-heated, if necessary, in a coil 11 and entering at 12 at the bottom of the reactor by flying through a sole 13. In that way, by injecting an adequate gaseous flow, the alloy particles are separated from one another by means of a fluid consisting of the organic halide mixed with an inert gas which is nitrogen.

Further the reactor comprises a stirring device (not represented on the drawing) for keeping the entire fluidised bed in a thorough agitation, in order to avoid the creation of preferential paths through the bed.

The reactor shown in FIG. 1 is made for keeping the optimum fluidization rate, inter alia by providing baffles. It may work continuously or discontinuously, whereby the feeding charge may be, as seen, introduced and removed pneumatically. The selection of the sole 13 of the reactor (e.g. sintered stainless steel) is very important because the sole should provide for the most uniform possible feeding with support gas (RX). At the outlet of the reactor 6, the gaseous mass comprising the excess halide (RX) and the product or products of reaction ($R_n Sn X_{4-n}$) is fractionated into its components either by a condenser or by a liquid-gas counter-current exchanger (not shown) where the reaction products are dissolved in a volatile solvent such as acetone. These separations are easy because of the very great differences of physical constants. The excess halide (RX) is recycled or stocked. The dilution of organic halide by means of an inert gas is useful if the reaction kinetics is too quick. The pressure in the reaction zone may be atmospheric or higher or lower than atmospheric, the atmospheric pressure being generally preferred.

The process based on the principle of a particle separation by reaction fluid allows an extremely quick synthesis of organo-tin halides because the kinetics of the whole process is only limited by that of the reaction and no longer by physical restrictions connected to diffusion and which always cause a very great slowness.

On the other hand, by keeping a constant fluidization level, welding of the particles together is avoided and this permits the exhausted alloy to be withdrawn easily.

Thus, the major drawbacks of the mixed bed process are avoided.

The whole duration of the process may thus consiserably be reduced on industrial scale (about 20 to 50 times).

The flow rates of organic halide gas, more particularly alkyl halide, in mixture with an inert gas are of course of an entirely different order of magnitude than the flow rates of gas used in the fixed bed process, not only because consumption is much higher but also because the gas should maintain the fluidization rate. According to the particle size, the flow rates vary from 5 to 40 l/hour.cm2.

The invention is now described referring to the following examples.

EXAMPLE 1

20 kg of the tin-copper alloy $Cu_3Sn$ (copper and tin content respectively 60% and 40% by weight) having a particle size of about 50 microns are mixed with 20 kg of sand having a particle size of about 0.1 mm.

This mixture is fluidised by means of a nitrogen stream at a temperature of 320° C in a reactor having a diameter of 30 cm. As soon as the fluidisation by the nitrogen is achieved the bed is stirred by means of a steel agitator, rotating at a rate of about 150 cycles/min., so as to avoid the creation of preferential paths through the bed.

As soon as these conditions are atteined one adds to the nitrogen stream maintaining the fluidization, a partial pressure of methylchloride (about 0,3 atm.) At the starting of the operation the gas ($N_2$ + $Ch_3Cl$) is preheated in order to maintain the temperature of the alloy. When the reaction has started, on the contrary, the gas is introduced cold having regard the exothermicity of the reaction. After two hours of processing the bed is exhausted of tin and one collects about 12 kg of $(CH_3)_2SnCl_2$ which means a yield of 80% with respect to the tin content of the alloy.

EXAMPLE 2

20 kg of a powdered copper-tin alloy, having a copper and tin content of respectively 40% and 60% by weight, are used. The particle size of this powder is about 50 micron. The powder is obtained by atomization, the alloy being too soft to be milled.

This alloy charge is mixed with 20 kg of sand having a particle size of about 0,1 mm.

Proceeding as indicated in example 1 one obtains after 2 hours of processing 18 kg of $(CH_3)_2SnCl_2$.

This also corresponds to a yield of 80% with respect to the tin content of the alloy.

What I claim is:

1. A process for synthesizing organo-tin halides of the formula $R_nSn\ X_{4-n}$, wherein R represents an alkyl or aryl radical, X represents a halogen atom and n represents an integer equal to 1, 2 or 3, by reacting an organic halide of the formula RX, wherein R and X have the meanings indicated above, in the gaseous phase at a temperature between 300° and 400° C, with finely divided solid alloy particles consisting of tin and a catalyst of the group consisting of copper, gold and silver, characterized in that contact of the solid alloy particles, having a particle size between about 50 and 250 microns, with one another is avoided by separating said particles in a fluidized bed by means of a fluid, comprising said organic halide mixed with an inert gas, at a flow rate of 5 to 40 l/hour-cm2, by admixing refractory particles with said alloy particles and by thoroughly stirring the fluidized bed.

2. The process as claimed in claim 1, wherein said inert gas is nitrogen.

3. The process as claimed in claim 1, wherein said organic halide is methylchloride $Ch_3Cl$ and said organo-tin halide is dimethyldichlorostannane $(CH_3)_2SnCl_2$.

4. The process as claimed in claim 1, wherein the alloy of tin is an alloy of copper and tin having a tin content of more than about 40% by weight.

5. The process as claimed in claim 1, wherein the tin content of the alloy is between about 40% and about 60% by weight.

6. The process as claimed in claim 1, wherein the reaction is performed at a temperature of about 350° C.

7. The process as claimed in claim 1, wherein the refractory particles are constituted of sand, silica or alumina having a particle size of about 0.1 mm.

8. The process as claimed in claim 1, wherein the particle size of said solid alloy particles is about 50 microns.

* * * * *